US012773552B2

(12) United States Patent
Leuthardt et al.

(10) Patent No.: US 12,773,552 B2
(45) Date of Patent: Oct. 27, 2026

(54) SYSTEMS AND METHODS FOR REDUCING INFLAMMATION IN THE CENTRAL NERVOUS SYSTEM

(71) Applicant: Washington University, St. Louis, MO (US)

(72) Inventors: Eric Leuthardt, St. Louis, MO (US); Anna Huguenard, St. Louis, MO (US)

(73) Assignee: Washington University, St. Louis, MO (US)

( * ) Notice: Subject to any disclaimer, the term of this patent is extended or adjusted under 35 U.S.C. 154(b) by 166 days.

(21) Appl. No.: 18/698,815

(22) PCT Filed: Oct. 6, 2022

(86) PCT No.: PCT/US2022/045841
§ 371 (c)(1),
(2) Date: Apr. 5, 2024

(87) PCT Pub. No.: WO2023/059760
PCT Pub. Date: Apr. 13, 2023

(65) Prior Publication Data

US 2024/0399148 A1 Dec. 5, 2024

Related U.S. Application Data

(60) Provisional application No. 63/253,606, filed on Oct. 8, 2021.

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01); *A61N 1/0492* (2013.01); *A61N 1/36036* (2017.08)

(58) Field of Classification Search
CPC .............. A61N 1/36034; A61N 1/0456; A61N 1/0492; A61N 1/36036; A61N 1/36025
See application file for complete search history.

(56) References Cited

U.S. PATENT DOCUMENTS 10,130,809 B2 * 11/2018 Cartledge ................ A61N 1/18
10,232,178 B2 * 3/2019 Simon ................ A61N 1/36025
(Continued)

FOREIGN PATENT DOCUMENTS

EP 3100764 A1 12/2016
WO 2021099466 A2 5/2021
(Continued)

OTHER PUBLICATIONS

International Search Report and Written Opinion for Application No. PCT/US2022/045841, mailed Mar. 3, 2023 (18 pages).
(Continued)

*Primary Examiner* — Carl H Layno
*Assistant Examiner* — Heidi A Hilsmier
(74) *Attorney, Agent, or Firm* — Armstrong Teasdale LLP

(57) ABSTRACT

The present disclosure describes a system for transcutaneous auricular branch vagal nerve stimulation. Stimulation of the vagal nerve is configured to reduce inflammation in the central nervous system. The system includes a first electrode to be attached to a cymba of a patient's ear, a second electrode to be attached to a cavum of the patient's ear, and a flexible substrate to be bent over the ear to secure the system to the patient's ear.

19 Claims, 10 Drawing Sheets

(56) References Cited

U.S. PATENT DOCUMENTS

| | | | | |
|---|---|---|---|---|
| 10,967,182 | B2 | 4/2021 | Khodaparast et al. | |
| 11,590,341 | B2 * | 2/2023 | Errico | A61N 1/36021 |
| 11,944,807 | B2 * | 4/2024 | Simon | A61N 1/0492 |
| 12,465,718 | B2 * | 11/2025 | Wetmore | A61M 21/00 |
| 2013/0245712 | A1 | 9/2013 | Simon et al. | |
| 2019/0151604 | A1 | 5/2019 | Harper et al. | |
| 2020/0086108 | A1 | 3/2020 | Simon et al. | |
| 2020/0238085 | A1 | 7/2020 | Khodaparast et al. | |
| 2020/0338348 | A1 | 10/2020 | Honeycutt et al. | |
| 2022/0370786 | A1 * | 11/2022 | Atkin | A61N 1/36036 |
| 2025/0281742 | A1 * | 9/2025 | John | A61N 1/0456 |

FOREIGN PATENT DOCUMENTS

| | | | | |
|---|---|---|---|---|
| WO | WO-2022221644 | A2 * | 10/2022 | A61N 1/0456 |
| WO | WO-2022221858 | A2 * | 10/2022 | A61N 1/36014 |

OTHER PUBLICATIONS

European Extended Search Report for Application No. 22879265.1, dated Apr. 1, 2025 (7 pages).

* cited by examiner

SYSTEMS AND METHODS FOR REDUCING INFLAMMATION IN THE CENTRAL NERVOUS SYSTEM

CROSS REFERENCE TO RELATED APPLICATIONS

This application is a national stage filing of International Application No. PCT/US2022/045841 filed Oct. 6, 2022, which claims the benefit of and priority to U.S. Provisional Patent Application No. 63/253,606, filed Oct. 8, 2021, entitled "SYSTEMS AND METHODS FOR REDUCING INFLAMMATION IN THE CENTRAL NERVOUS SYSTEM," which are hereby incorporated by reference in their entirety.

STATEMENT REGARDING FEDERALLY SPONSORED RESEARCH OR DEVELOPMENT

This invention was made with government support under NS128307 awarded by the National Institutes of Health. The government has certain rights in the invention.

BACKGROUND

The present disclosure generally relates to systems and methods of inflammation in the central nervous system.

The traditional view of the brain as an immune privileged organ has been definitively revised. In fact, although the response of the brain to specific harmful stimuli is distinct from that seen in other organs, neuroinflammation processes frequently occur in the brain either autonomously or in combination with other types of injury. Indeed, inflammatory mechanisms are often engaged within the context of degenerative, vascular, and traumatic injuries, thus contributing to further damage and poor outcomes. Key features of central nervous system inflammation include the development of edema, glial activation, modulation of the expression of the major histocompatibility complex, the synthesis of acute phase proteins, activation of the complement system, the synthesis of inflammatory mediators, the expression of adhesion molecules, and the invasion of immune cells. Moreover, most of the cellular and molecular pathways underlying neuroinflammation show both deleterious and protective actions on neurons, mainly depending on the stage of the injury. This makes it difficult to implement selective pharmacological strategies aimed at confining the detrimental effects of inflammation without interfering with its protective action.

Neuroinflammation in the brain drives numerous disease states. Pharmacologic approaches have limited penetration in the brain and also have numerous systemic off target effects that are clinically suboptimal. Having a bioelectric approach that harnesses the bodies endogenous neurologic immunosuppressive circuits provides a method to drastically improve treatment of numerous diseases where neuro-inflammation is a common pathologic mechanism.

Vagus nerve stimulation (VNS) has emerged as a tool to promote and accelerate neuroplasticity in both healthy and injured brains, attributed in part to the release of plasticity-promoting neuromodulators at the cellular level. The vagus nerve is a mixed-fiber nerve that affects many upstream cortical and subcortical structures. Non-invasive transcutaneous auricular VNS (taVNS) has been demonstrated to improve post-stroke functional recovery. Despite encouraging preclinical and clinical results, the neural response to non-invasive VNS and the mechanism through which it affects functional motor recovery remain poorly understood in humans. This gap has limited the advancement of this therapeutic strategy.

BRIEF DESCRIPTION

In a first aspect, a system for transcutaneous auricular branch vagal nerve stimulation is provided. The system includes a first electrode to be attached to a cymba of a patient's ear. The system also includes a second electrode to be attached to a cavum of the patient's ear. The system further includes a flexible substrate to be bent over the ear to secure the system to the patient's ear.

In a second aspect, a method for transcutaneous auricular branch vagal nerve stimulation to reduce inflammation in the central nervous system is provided. The method includes attaching a stimulation device to the patient's ear, wherein the stimulation device includes a first electrode to be attached to a cymba of a patient's ear and a second electrode to be attached to a cavum of the patient's ear. The method also includes stimulating a cutaneous distribution of a patient's vagus nerve within the patient's ear with a nerve stimulating signal via the stimulation device.

In a third aspect, a disposable device for transcutaneous auricular branch vagal nerve stimulation to reduce inflammation in the central nervous system is provided. The device includes an electrical stimulation device including two electrodes and a battery. The electrical stimulation device is configured to provide an electrical current to a patient's vagus nerve with an electrical signal for twenty minutes. The electrical signal is configured to stimulate a cutaneous distribution of a patient's vagus nerve within the patient's ear with a nerve stimulating signal. The device further includes an adhesive to attach the device to the patient's ear.

BRIEF DESCRIPTION OF THE DRAWINGS

Those of skill in the art will understand that the drawings, described below, are for illustrative purposes only. The drawings are not intended to limit the scope of the present teachings in any way.

Figure 1A:
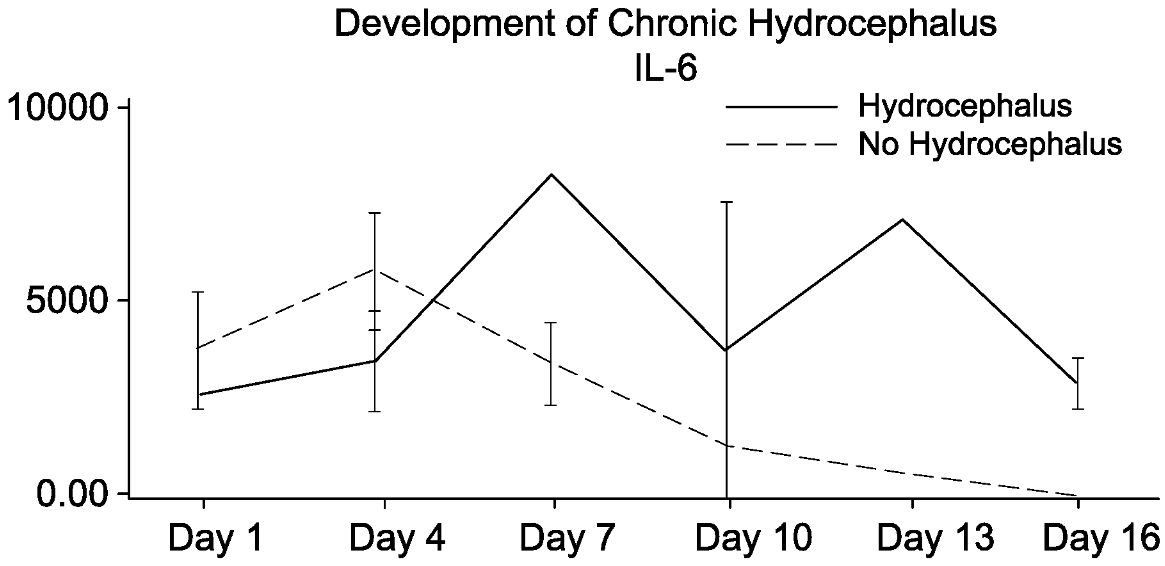
FIGS. 1A-1D illustrate graphs of inflammatory cytokines associated with SAH induced hydrocephalus and vasospasm.
Figure 1B:
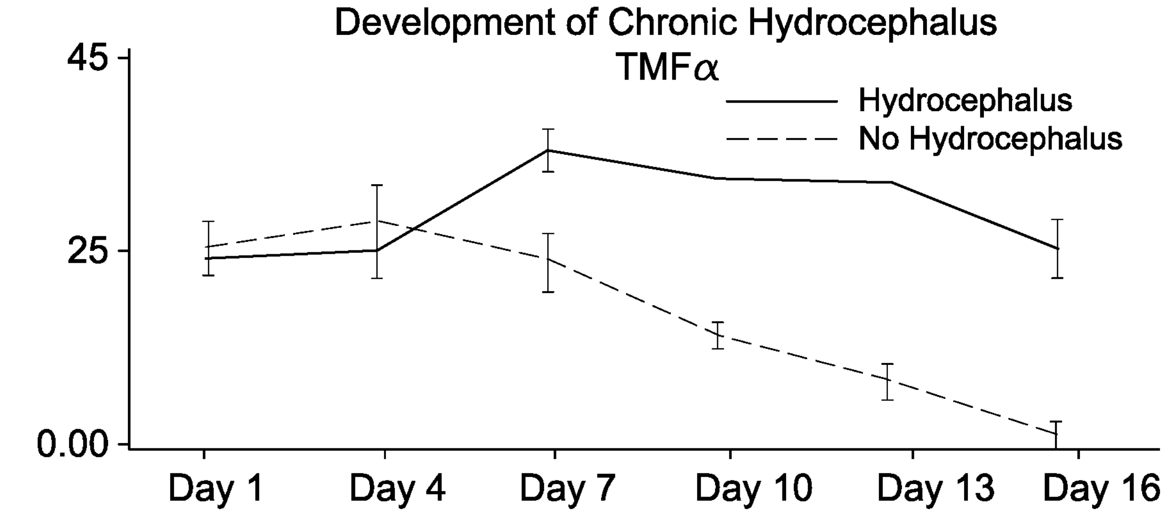
Figure 1C:
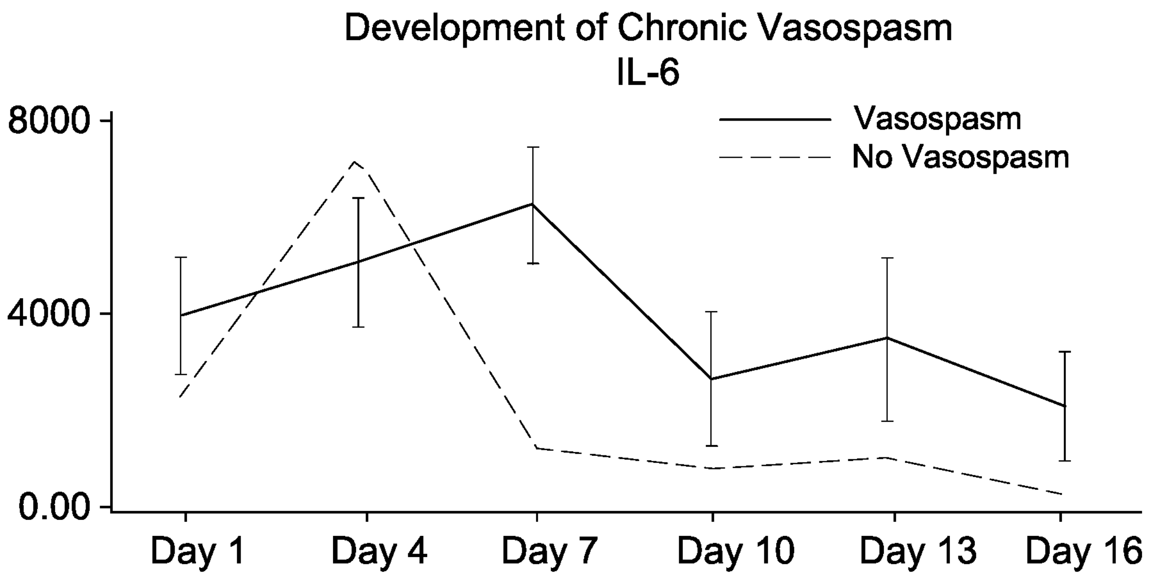
Figure 1D:
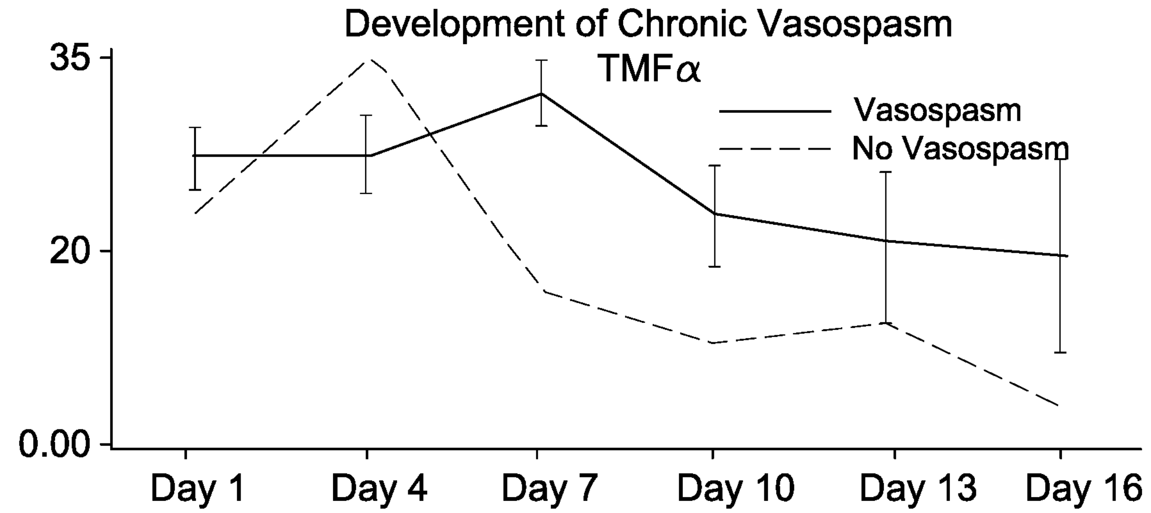

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Among the various aspects of the present disclosure is the provision of systems and methods for reducing inflammation using non-invasive transcutaneous auricular vagus nerve stimulation (taVNS).

The Central Nervous System (CNS) may be the target of several chronic inflammatory-related pathologies where the inflammatory component acts either as a primary cause of the disease or as a secondary outcome of the tissue damage. Key neurodegenerative diseases that inflammation plays a role in include, but are not limited to, Alzheimer's Disease, Parkinson's Disease, Huntington's Disease, and Amyotrophic Lateral Sclerosis.

Alzheimer's Disease (AD) belongs to a wide clinical spectrum of dementias. Pathological alterations in AD include the extracellular deposition of amyloid-beta (A13) protein and the intracellular accumulation of neurofibrillary tangles generated by an abnormal hyperphosphorylated tau protein. These aggregates of proteins are perceived as a danger signal by the immune system, which triggers an inflammatory response with the aim of providing tissue repair mechanisms. Within this context, microglia switch from their deactivated phenotype, associated with the production of anti-inflammatory and neurotrophic factors, to an activated phenotype that serves to promote an inflammatory response and to further engage the immune system and initiate tissue repair. The above switch is evidenced by the observation that activated microglia surrounding senile plaques stain positive for several inflammatory markers including Major Histocompatibility Complex (MHC) class II, cyclooxigenase-2 (COX-2), monocyte chemoattractant protein-1 (MCP-1), tumor necrosis factor-α (TNF-α), interleukin (IL)-113, and IL-6. The detection of A13 by microglia, and their subsequent activation is mediated by several Pattern-recognition Receptors (PRRs), including Toll-like Recep-tors (TLRs), Receptors of Advanced Glycation end-products (RAGE), and Nod-like receptors (NLRs). These receptors, which usually bind to the so-called pathogen-associated molecular patterns ('stranger signals'), have recently been reported to respond also to endogenously derived molecules including those that may be formed as a consequence of pathogenic mechanisms like A13 accumulation. Ligation of PRRs leads to the activation of signal transduction pathways, which regulate multiple transcriptional and posttranscriptional processes, ultimately resulting in an increase of local inflammation that may further amplify neuronal death in AD. The production of inflammatory factors also stimulates astrocytes, which amplify proinflammatory signals and neurotoxic effects. Microglia also show an impaired capacity for clearance of extracellular tau protein. Tau phosphorylation and dysfunction in turn induces the release of chemokines, including fractalkine (CX3CL1), which maintains microglia in a quiescent state and contributes to perpetuating a condition of uncontrolled dysfunctional inflammation. Together with microglia, astrocytes are also responsible for A13 clearance. However, chronic exposure to amyloid plaques may lead to a condition of astrogliosis and create a pro-inflammatory state through the release of IL-1b, IL-6, and S100B.

Parkinson's disease (PD) is a neurological disorder characterized by typical motor features including rest tremor, bradykinesia and rigidity. Its onset follows the loss of dopaminergic neurons in the substantia nigra. The role of inflammation in PD was first observed almost 30 years ago when inflammatory molecules were found in postmortem brains of PD patients. Under pathological conditions, alpha-synuclein (α-Syn) can undergo numerous mutational changes, including phosphorylation, oxidation, glycation, and nitrosylation. The altered forms of α-Syn induce microglia activation and phagocytosis. Activated microglia in turn release pro-inflammatory mediators inducing apoptosis, including TNF-α, IL-1ß, IL-6, chemokines, Regulated on Activation, Normal T Cell Expressed and Secreted (RANTES), MCP-1, C-X-C motif chemokine 10 (CXCL-10), and macrophage inflammatory protein-1α (MIP-1α). Activated microglia also induces a pro-inflammatory transformation in astrocytes. In addition to the transformation of microglia and astrocytes, the aggregates of α-Syn trigger an immune response that modifies the structure of proteasomes into so-called immune-proteasomes. Proteasomes are central regulatory hubs for intracellular signaling while immune-proteasomes are specialized types of proteasomes involved in shaping adaptive immune responses. Although the role of immune-proteasomes in neuroinflammation and PD progression has not been clarified, it is known that i-proteasomes have more enzyme domains, stronger enzymatic activity, and a greater capacity to degrade the α-synuclein proteins and orientate the MHC molecules to mediate inflammation/immune reaction. This is in line with the assumption that both innate and adaptive immunity are engaged, through the induction of MHC-class II expression by microglial cells, which can drive the proliferation and activation of CD4+ T cells and the secretion of interferon IFN-γ and TNF-α. Moreover, an increased production of prostaglandins (PGE2) and complement cascade proteins together with the activation of the humoral adaptive immune system has also been highlighted in PD pathogenesis. Specific hallmarks of neuroinflammation in PD also include excitotoxicity and oxidative stress. Excitotoxicity plays a significant role in linking inflammation and neurodegeneration in PD, as pro-inflammatory cytokines, such as IL-1β and TNF-α, have been shown to up-regulate glutamate synthesis and glutamate receptor activity in the brain. On the other hand, oxidative stress is the result of the production of free radicals, which in PD is exacerbated by neuroinflammation, dopamine degradation, mitochondrial dysfunction, aging, glutathione depletion, and high levels of iron or Ca2+.

Huntington's Disease (HD) is an inherited neurodegenerative disease characterized by progressive motor, behavioral and cognitive decline. A role of inflammation in the pathogenesis of HD has been evidenced by recent postmortem and animal studies. Both innate and adaptive immunity are involved in the pathogenesis of HD. Mutant huntington is expressed not only by neurons but also by microglia and astrocytes and is responsible for the activation of a sterile inflammatory process. Microglial activation and astrocytosis in HD result in increased production of inflammatory mediators including IL-6, IL-8, TNF-α, MCP-1/CCL2, IL-10, and matrix metal-loproteinase-(MMP-) 9.

Amyotrophic Lateral Sclerosis (ALS) is a progressive adult-onset neurodegenerative disease that primarily affects upper and lower motor neurons, but also frontotemporal and other regions of the brain. A role of neuroinflammation in the pathogenesis of ALS, mainly through a mechanism of glial activation, has recently been suggested. Aggregation of Superoxide Dismutase (SOD) 1 may activate microglia in a way similar to that observed for Aβ and α-Syn in AD and PD respectively. Along with the evidence sustaining an active role also for astrocytes in the induction and propagation of motor neuron loss in ALS, there is the observation that astrocytes from SOD1 mutant mice produce Fas ligands (FasL), which are mediators of neuronal death. Oxidative stress also plays a significant role in the pathogenesis of ASL. Signs of oxidative stress in mitochondria and protein aggregates of motor neurons correlate with the activity of the RAGE axis, the activation of which triggers an increase in proinflammatory molecules, oxidative stressors and cytokines. Finally, the role of the immune system in ALS pathogenesis is also evidenced by the association between the presence of functional variants of the human CX3CR1 gene (fractalkine receptor) and a shorter survival time in ALS patients. The human CX3CR1 gene influences the migration of leukocytes and may also play a role in microglial migration.

Inflammation also plays a role in cerebrovascular diseases. Cerebrovascular diseases include ischemic stroke, accounting for 80% of all cerebral events, and cerebral hemorrhage, which accounts for the remaining cases and can be subdivided into Intracerebral Hemorrhage (ICH) and Subarachnoid Hemorrhage (SAH). According to some recent research, acute ischemic stroke should be redefined as a thrombo-inflammatory disorder rather than a merely thrombotic disorder, as the immune response to acute ischemic stroke represents an important part of its pathogenesis. In fact, although the development of a thrombus is the main causal event leading to acute ischemic stroke, some evidence suggests that molecules involved in platelet adhesion and activation (glycoprotein (GP) Ib, collagen receptor GPVI, and coagulation factor XII) are multifunctional, as they are able to trigger and orientate inflammatory processes. Further evidence of the role of inflammation in acute ischemic stroke has come from the observation that murine models lacking T-lymphocytes are protected from the occurrence of acute ischemic cerebral events. Acute cerebral ischemia itself is associated with the augmented activity of platelets, leading to increased thrombogenesis and embolization. Both innate and acquired immune systems contribute to the inflammatory response related to acute cerebral ischemia. Acute ischemic stroke causes both a local inflammatory reaction and a variety of innate immune responses in the brain where antigen-presenting cells play a significant role. Studies on neurons, oligodendrocytes, astrocytes, and microglia exposed in vitro to acute ischemia have demonstrated that a variety of inflammatory mediators may be released by these cells. The expression of TNF-α following acute cerebral ischemia causes the release of several adhesion molecules acting on leukocytes. Other effects of acute ischemic stroke include the release of IL-1, factor VIII/von Wille-brand factor, platelet-activating factor, endothelin and nitric oxide, the suppression of the thrombomodulin-protein C-protein S system, the reduction of levels of tissue-plasminogen activator, and the secretion of plasminogen activator inhibitor-1. Furthermore, other substances such as interferon-gamma and IL-4 have the capacity to enhance the action of the above-described inducers of inflammation. Finally, IL-1, TNF-α, transforming growth factor (TGF)-1 beta, and prostaglandins may promote the secretion of IL-6, another crucial inflammatory mediator. The existence of an association between systemic inflammation and unfavorable ischemic stroke outcome has been broadly demonstrated. Notable scientific research on experimental models of cerebral ischemia, and observational studies on subjects with acute ischemic stroke have revealed that systemic inflammation may worsen the short and long-term outcome of an acute ischemic brain lesion. IL-1 also plays a key role in promoting inflammatory response after acute ischemic stroke. In an experimental model of mice lacking both IL-1a and IL-1b, volumes of cerebral ischemia were reduced when compared with acute ischemic strokes occurring in wild-type mice and in mice lacking either IL-1a or IL-1b solely. The balance between pro-inflammatory and anti-inflammatory responses has been recognized as a crucial factor conditioning the outcome of the ischemic lesion. The plasma levels of cytokines such as TNF-α and IL-1 1 may vary according to the etiological subtype of ischemic stroke.

Intracranial aneurysms are common, with 3-5% of all adults harboring at least one. The resulting subarachnoid hemorrhage (SAH) from ruptured aneurysms accounts for 5-10% of all strokes worldwide, culminating in a total of 600,000 new cases per year. SAH is a major driver of mortality and morbidity, with 10-25% of patients dying following SAH and an additional 30% of patients suffering permanent disability. While the immediate sequelae of SAH can include risk for re-rupture, elevated intracranial pressure, and acute hydrocephalus, secondary injury is a major driver of morbidity as mediated by early brain injury, cerebral vasospasm, delayed cortical ischemia, and chronic hydrocephalus. Targeting the post-hemorrhage period with the goal of reducing these secondary sequelae from SAH is an important mechanism for improving outcomes in SAH patients.

Vagus nerve stimulation (VNS) has been studied as a novel method of reducing inflammation. The vagus nerve, which is comprised of 80% afferent fibers and 20% efferent fibers, is the main visceral sensory nerve and innervates many organs throughout the body. Stimulating the vagus nerve is typically performed using surgically implanted cuff electrodes—encircling the left vagus nerve within the carotid sheath—that are connected to a pulse generator implanted in the left side of the patient's chest. The left vagus nerve is used because it has fewer efferent fibers descending to the heart than the right vagus nerve, making it a safer site for stimulation. VNS has been proven effective as a treatment for intractable epilepsy and treatment-resistant depression, and has recently been investigated for several neurological injuries such as stroke and traumatic brain injury.

Substantial work has demonstrated that molecular products of infection or injury activate sensory neurons traveling to the brainstem in the vagus nerve. The arrival of these incoming signals generates action potentials that travel from the brainstem to the spleen and other organs. This culminates in T cell release of acetylcholine, which interacts with α7 nicotinic acetylcholine receptors (α7 nAChR) on immunocompetent cells to inhibit cytokine release in macrophages (REF). This neural-immunomodulatory circuit referred to as the "cholinergic anti-inflammatory pathway" presents opportunities for developing novel therapeutic strategies to treat inflammatory diseases. It has been successfully implemented in models of inflammatory conditions like induced neuroinflammation, cerebral ischemia/reperfusion, rheumatoid arthritis, sepsis, and inflammatory bowel diseases or colitis. Harnessing its anti-inflammatory effects, VNS has been used in a mouse model of cerebral aneurysms and SAH. Pre-treatment with VNS has not only reduced the rupture rate of intracranial aneurysms, but also reduced the grade of hemorrhage if rupture occurred and improved survival and outcome after SAH. There has not been any work examining the effect of VNS on SAH in humans.

Historically, VNS was performed exclusively by surgical cervical neck dissection and placement of a cuff electrode directly around the nerve within the carotid sheath. Alternatively, VNS can be accomplished non-invasively by stimulating the auricular branch of the vagus nerve as it courses through the external ear, obviating the morbidity of a surgical procedure and allowing rapid deployment of the intervention in critically ill patients. The external ear is an ideal target for non-invasive stimulation of the vagus nerve, where the auricular branch travels in the concha of the ear. This transcutaneous auricular approach has demonstrated good efficacy, with minimal morbidity.

The systems and methods described herein propose a fully disposable integrated stimulator system that is affixed to the ear and stimulates specific cutaneous distribution of the vagus nerve in the ear (i.e. cymba and concha). Having a system that could be use adhesive hydrogels that both enable mounting in the ear and optimal bioelectric couple with the skin would best enable clinical treatment. The system could be used to reduce inflammatory cytokines, such as IL6 and TNF-alpha, that are associated with pathologic inflammation the brain. Examples of specific inflammatory scenarios include subarachnoid hemorrhage, multiple sclerosis, Alzheimer disease, Parkinson disease, Amyotrophic lateral sclerosis, Cerebral ischemia, Traumatic brain injury, autoimmune disorders, meningitis, encephalitis, depression and psychiatric disorders, and epilepsy.

In some aspects, the method includes administering vagal nerve stimulation (VNS) to a patient in need. VNS can be accomplished non-invasively by stimulating the auricular branch of the vagus nerve in the ear. This transcutaneous auricular approach has demonstrated good efficacy. In one aspect, the transcutaneous stimulation of the auricular branch of the vagus nerve is implemented using a portable TENS (transcutaneous electrical nerve stimulation) unit connected to two ear clip electrodes positioned in an ear of the subject. Without being limited to any particular theory, the external ear is an effective position for non-invasive stimulation of the vagus nerve, where the auricular branch travels in the pinna of the ear. In one aspect, the ear clips used for the VNS treatment are positioned along the concha of the ear. In another aspect the device can be wholly configured to be affixed to the ear which include the electrode, power, electronics, and wearable form factor.

Generally, a safe and effective amount of vagal nerve stimulation (VNS) is, for example, an amount that would cause the desired therapeutic effect in a subject while minimizing undesired side effects.

In various aspects, the vagus nerve stimulation is delivered as characterized by a VNS parameter comprising at least one of a stimulation frequency, a pulse-width, a current intensity, and any combination thereof. The VNS parameters may be any suitable value without limitation. In some aspects, the stimulation frequency ranges from about 10 Hz to about 50 Hz. In some aspects, the stimulation frequency is selected from 20 Hz, 30 Hz, or 40 Hz. In some aspects, the pulse-width ranges from about 100 μs to about 500 μs. In some aspects, the pulse-width is selected from 100 μs, 250 μs, and 500 μs. In some aspects, the current intensity ranges from about 0.5 mA below a perceptual threshold to about the perceptual threshold, wherein the perceptual threshold comprises a current intensity sufficient to elicit a tingling sensation in the subject.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

Optional" or "optionally" means that the subsequently described event or circumstance may or may not occur, and that the description includes instances where the event occurs and instances where it does not.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

FIGS. 1A-1D illustrate graphs of inflammatory cytokines associated with SAH induced hydrocephalus and vasospasm. The graphs illustrate average levels of two pro-inflammatory cytokines, IL-6 and TNF-α, overtime in patients hospitalized with SAH. Plasma levels of IL-6 CSF levels of IL-6 (Shown in FIG. 1A) and TNF-α (Shown in FIG. 1B) trend higher in patients who develop hydrocephalus (n=2) starting on hospital day 7 compared with patients without chronic hydrocephalus (n=4). Similarly, CSF levels of IL-6 (Shown in FIG. 1C) and TNF-α (Shown in FIG. 1D) trend higher in patients with vasospasm (n=5) starting on hospital day 7 compared with patients without evidence of radiographic vasospasm on serial vascular imaging (n=1). Error bars represent S.E.M (standard error of the mean).

There is growing evidence that systemic and local inflammation may promote aneurysm formation and rupture as well as lead to poorer outcomes following aneurysmal rupture. Following SAH, blood within the subarachnoid space triggers both local, as measured by inflammatory markers in the cerebrospinal fluid (CSF), and systemic inflammatory responses, as measured by inflammatory markers in the blood. Prior work has examined identified cytokines including IL-11, IL-4, IL-8, IL-10, IL-18, and IL-33 following SAH in animal and human studies. A key driver of SAH induced inflammation are cytokines IL-6 and TNF-α. Studies in canine and rabbit models of SAH demonstrate increased rates of vasospasm correlated with expression of IL-6 in the basilar artery, and CSF, respectively. Work performed in humans reveals elevated IL-6 in the blood, and CSF following SAH. In several studies, elevated IL-6 in the CSF was significantly correlated with development of vasospasm, delayed cortical ischemia, chronic hydrocephalus, and poorer overall outcomes following SAH. Similarly, studies in rodent and rabbit models of SAH found increased TNF-α was associated with vasospasm. In humans, elevated TNF-α in the blood and CSF have been demonstrated following SAH. Elevated TNF-α has been associated with vasospasm, hydrocephalus, and poor outcomes.

The pharmacological approaches to target inflammation following SAH have been unsuccessful. Numerous anti-inflammatory interventions have been trialed in humans to better understand, and eventually target, inflammatory pathways to improve outcomes after SAH. In smaller enrollment studies, there was promise of outcome improvement with Cyclosporin and steroids (methylprednisolone, hydrocortisone, and dexamethasone). Other medications demonstrated no impact on overall outcomes, like Clazosentan, Cilostazol, and IL-1 antagonists. In several meta-analysis studies looking at groups larger than 1000 patients, Simvastatin, Aspirin, non-steroidal anti-inflammatory medications, and thienopyrindines all demonstrated no improvement in outcomes. In summary, while some pathway-targeted pharmacological approaches have led to changes in secondary outcomes of vasospasm and delayed cerebral ischemia in clinical trials, these approaches have failed to produce an effective intervention that reliably improves outcomes in SAH patients. Thus, there is an urgent need to find a novel approach to more globally and meaningfully reduce inflammation in SAH to reduce patient morbidity.

Vagus nerve stimulation (VNS) has been studied as a novel method of reducing inflammation. The vagus nerve, which is comprised of 80% afferent fibers and 20% efferent fibers, is the main visceral sensory nerve and innervates many organs throughout the body. Stimulating the vagus nerve is typically performed using surgically implanted cuff electrodes—encircling the left vagus nerve within the carotid sheath—that are connected to a pulse generator implanted in the left side of the patient's chest. The left vagus nerve is used because it has fewer efferent fibers descending to the heart than the right vagus nerve, making it a safer site for stimulation. VNS has been proven effective as a treatment for intractable epilepsy and treatment-resistant depression, and has recently been investigated for several neurological injuries such as stroke and traumatic brain injury.

Substantial work has demonstrated that molecular products of infection or injury activate sensory neurons traveling to the brainstem in the vagus nerve. The arrival of these incoming signals generates action potentials that travel from the brainstem to the spleen and other organs. This culminates in T cell release of acetylcholine, which interacts with α7 nicotinic acetylcholine receptors (α7 nAChR) on immunocompetent cells to inhibit cytokine release in macrophages (REF). This neural-immunomodulatory circuit referred to as the "cholinergic anti-inflammatory pathway" presents opportunities for developing novel therapeutic strategies to treat inflammatory diseases. It has been successfully implemented in models of inflammatory conditions like induced neuroinflammation, cerebral ischemia/reperfusion, rheumatoid arthritis, sepsis, and inflammatory bowel diseases or colitis. Harnessing its anti-inflammatory effects, VNS has been used in a mouse model of cerebral aneurysms and SAH. Pre-treatment with VNS has not only reduced the rupture rate of intracranial aneurysms, but also reduced the grade of hemorrhage if rupture occurred and improved survival and outcome after SAH. There has not been any work examining the effect of VNS on SAH in humans.

Historically, VNS was performed exclusively by surgical cervical neck dissection and placement of a cuff electrode directly around the nerve within the carotid sheath. Alternatively, VNS can be accomplished non-invasively by stimulating the auricular branch of the vagus nerve as it courses through the external ear, obviating the morbidity of a surgical procedure and allowing rapid deployment of the intervention in critically ill patients. The external ear is an ideal target for non-invasive stimulation of the vagus nerve, where the auricular branch travels in the concha of the ear.

This transcutaneous auricular approach has demonstrated good efficacy, with minimal morbidity.

The systems and methods described herein propose a fully disposable integrated stimulator system that is affixed to the ear and stimulates specific cutaneous distribution of the vagus nerve in the ear (i.e. cymba and concha). Having a system that could be use adhesive hydrogels that both enable mounting in the ear and optimal bioelectric couple with the skin would best enable clinical treatment. The system could be used to reduce inflammatory cytokines, such as IL6 and TNF-alpha, that are associated with pathologic inflammation the brain. Examples of specific inflammatory scenarios include subarachnoid hemorrhage, multiple sclerosis, Alzheimer disease, Parkinson disease, Amyotrophic lateral sclerosis, Cerebral ischemia, Traumatic brain injury, autoimmune disorders, meningitis, encephalitis, depression and psychiatric disorders, and epilepsy.

The status quo for targeting the inflammatory response following SAH has been the development of pathway-specific anti-inflammatory pharmacologic agents. The work in this sector has centered around translating findings in animal models to larger prospective human trials. Despite promising mechanistic support, early animal data, and even improvement in deleterious secondary endpoints in humans (vasospasm, cerebral ischemia), there has not been success in identifying an effective targeted pharmacologic agent to improve morbidity in SAH patients. This research harnesses a broader endogenous neuro-immunologic system (i.e. cholinergic anti-inflammatory pathway) through a non-pharmacologic bioelectric approach to alter SAH inflammatory mediated morbidity. Using non-invasive electrical VNS stimulation to alter systemic and central inflammation is a seachange in methodological approach clinically. Given the low risk, low cost, and ubiquitous nature of portable stimulation devices and the lack of need for specialized training to apply the treatment, this novel technique that could rapidly scale to clinical environments across the globe.

In at least one study, SAH patients with vasospasm and hydrocephalus are shown to have elevated inflammatory cytokines. Patients with aneurysmal SAH with ventriculostomies were evaluated regarding the levels of CSF inflammatory cytokines depending on whether they developed chronic hydrocephalus or vasospasm. CSF specimens were taken every three days beginning within 24 hours of initial presentation. Consistent with prior literature, the patients who did developed chronic hydrocephalus requiring permanent shunting and vasospasm requiring procedural interventions had trends of higher CSF levels of the pro-inflammatory cytokines IL-6 and TNF-α than those who did not. These findings demonstrate the important role of IL-6 and TNF-α in key morbidities associated with SAH.

Figure 2A:
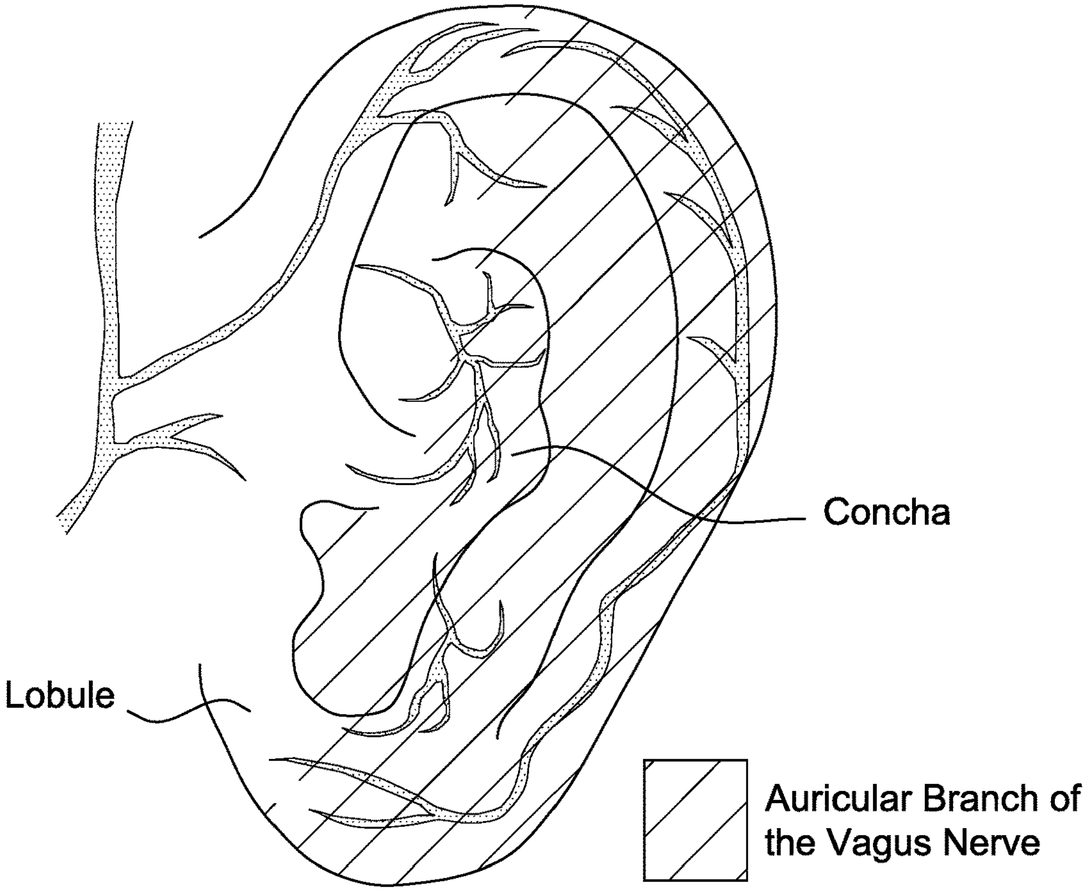
FIGS. 2A-D illustrate set-ups for and graphs of transcutaneous auricular branch vagal nerve stimulation.
Figure 2B:
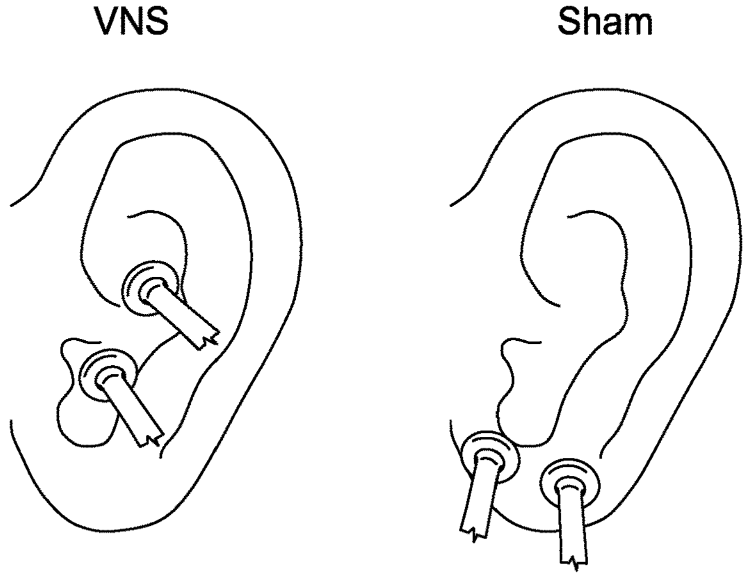
Figure 2C:
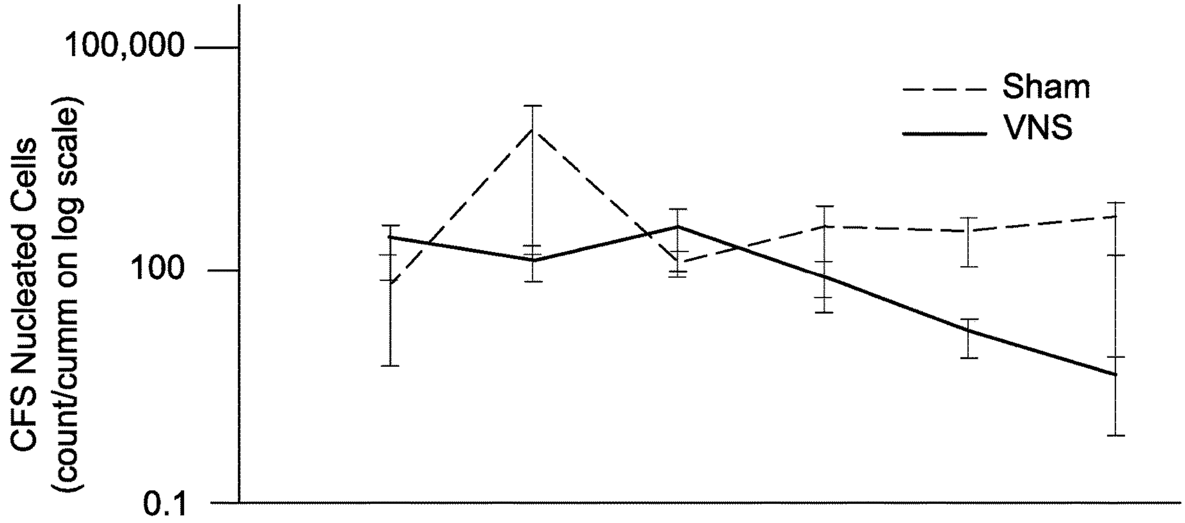
Figure 2D:
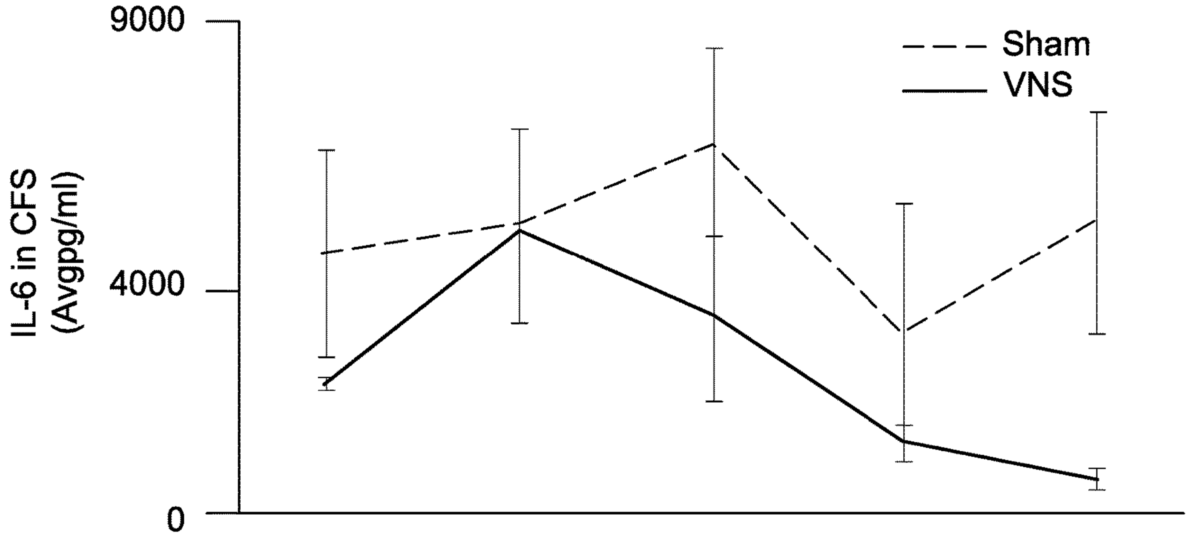
Figure 2E:
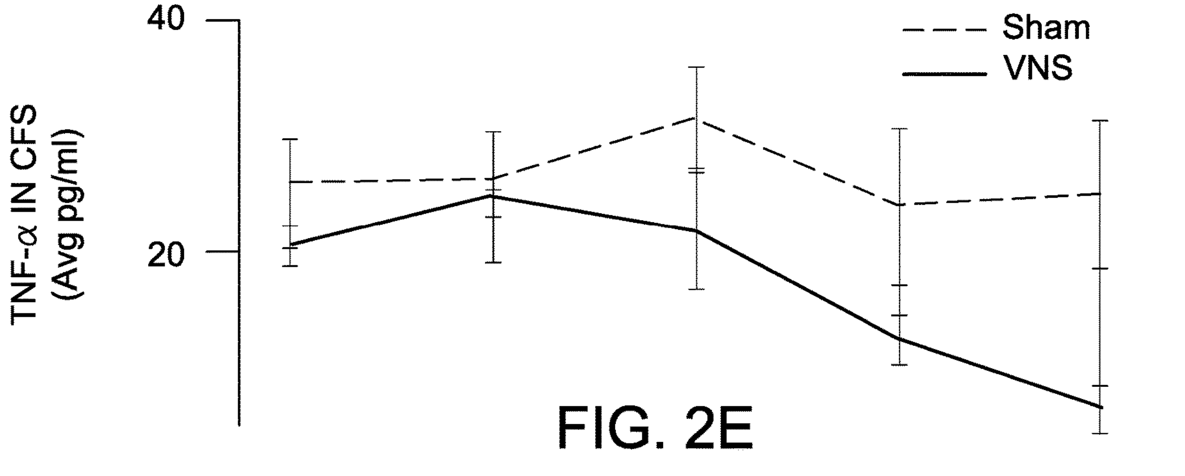

FIGS. 2A-2E illustrate set-ups for and graphs of transcutaneous auricular branch vagal nerve stimulation. FIG. 2A shows the cutaneous distribution of vagus nerve in the ear. FIG. 2B shows electrodes stimulating VNS and sham location on ear lobe. Average level of inflammatory markers in patients treated with VNS compared with sham. FIG. 2C illustrates CSF nucleated cell count trended lower in patients treated with VNS (VNS n=4, sham n=3). FIGS. 2D and 2E illustrates levels of IL-6 and TNF-α, respectively, in the CSF trend lower in patients treated with VNS after hospital day 4, where VNS n=3 and sham n=3. Error bars represent S.E.M. T-test performed at each time point for each, * indicates $p<0.05$.

In another study, transcutaneous VNS stimulation is shown to reduce inflammatory cytokines in SAH patients. Patients admitted following an acute, spontaneous (non-traumatic) SAH were screened for enrollment and randomized to a treatment arm, initial samples of blood and CSF (via a venctriculostomy) were collected prior to definitive intervention for the aneurysm. The patient began either VNS or sham stimulation within 24 hours of study enrollment, and continued to receive the treatment twice daily during their stay in the intensive care unit. The treatment consisted of a portable TENS (transcutaneous electrical nerve stimulation) unit connected to two ear clips, applied to the left ear during treatment periods. For VNS treatment, these ear clips are placed along the concha of the ear (shown in FIGS. 2A & 2B), while in sham treatments the clips are placed along the ear lobe (shown in FIG. 2B) to avoid stimulation of the auricular vagus nerve from tactile pressure alone in the absence of current. Stimulation parameters were as follows: 1) VNS Treatment Arm: 20 minutes, 20 Hz, 250 ms pulse width, 8 mA. 2) Sham Stimulation Arm: 20 minutes, no current applied. In this cohort of patients, when compared to sham stimulation, VNS stimulated patients had lower CSF nucleated cell count, and lower pro-inflammatory cytokine (IL-6 and TNF-α) levels (shown in FIGS. 2C, 2D, and 2E). This supports that taVNS can induce a measurable cellular/cytokine in SAH patients.

Figure 3A:
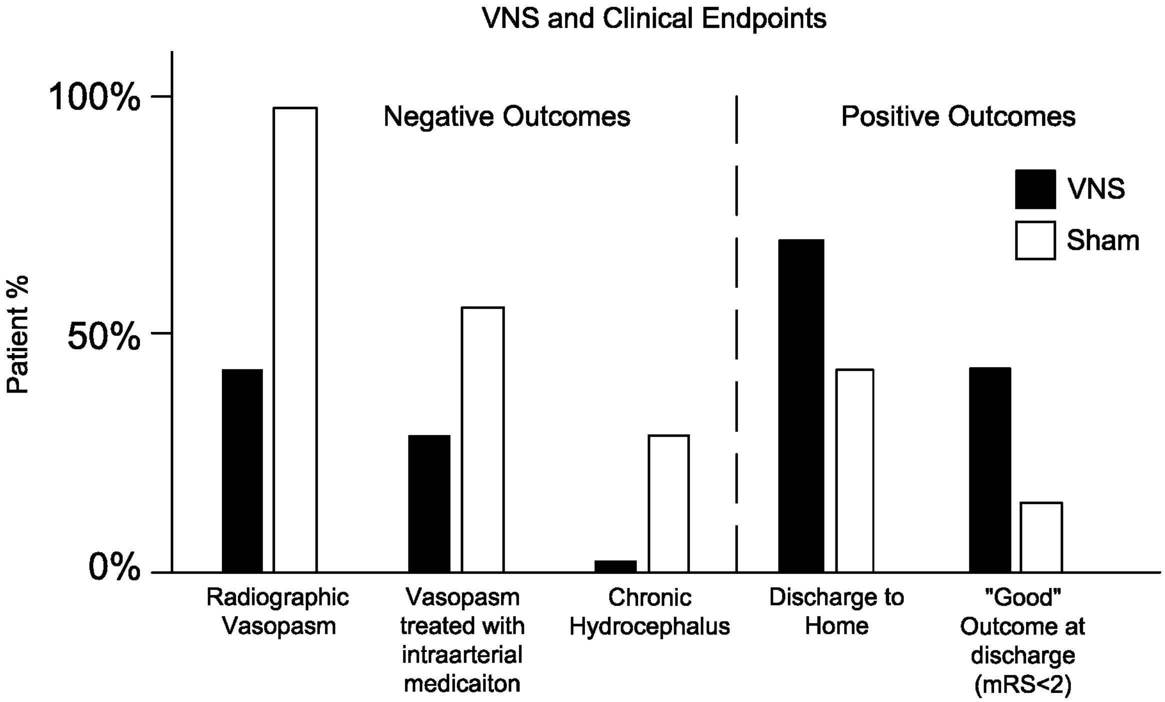
FIGS. 3A-B illustrate graphs of transcutaneous auricular branch vagal nerve stimulation (taVNS) associated with improvements in clinical outcomes.
Figure 3B:
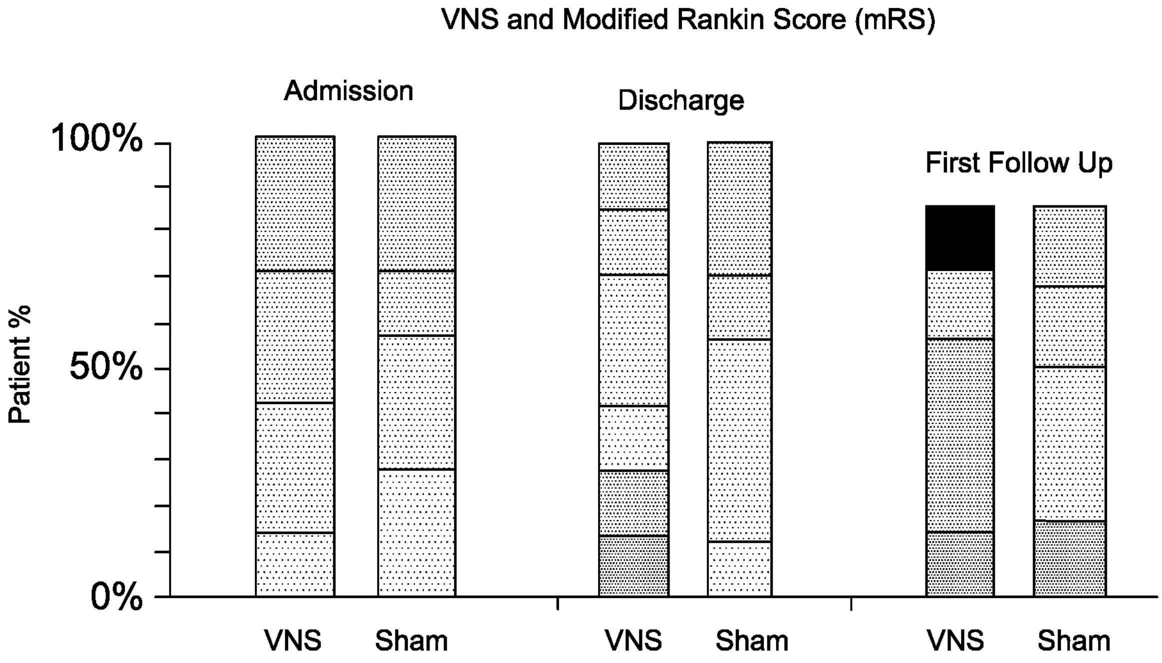

FIGS. 3A and 3B illustrate graphs of transcutaneous auricular branch vagal nerve stimulation (taVNS) associated with improvement in clinical outcomes.

taVNS has been shown to improve clinical outcomes in SAH patients. In addition to data showing that taVNS treatment reduces inflammatory cytokines compared to sham treatment, there are also encouraging trends in in key endpoints that define morbidity in the SAH population. In a group of patients, radiographic vasospasm and chronic hydrophalus were reduced with VNS compared to sham. Also, positive endpoints of increased likelihood for discharging to home and good functional outcomes appear to be enhanced with VNS (shown in FIG. 3A). This trend in improvement in the overall function can be further see in the evolution of |Modified Rankin score (mRS across the patients' progression through care. The mRS was evaluated for three time points for those treated with VNS and sham: 1) admission, 2) discharge, and 3) first outpatient follow up. Of note, a "good outcome consists of green shades representing mRS 0-2. The proportion of good outcomes grows far greater in the VNS treated group over time (shown in FIG. 3B).

Inflammatory response also plays a role in damage induced by the presence of intracranial hemorrhage (ICH). Neutrophils, monocyte/macrophages, microglia, and several cytokines act as mediators of the brain inflammation following ICH, via the infiltration of brain parenchyma by neutrophils and monocytes/macrophages, the activation of microglia, and the secretion of a variety of cytokines. These events lead to the subsequent activation of cytotoxic, excitotoxic, oxidative and inflammatory pathways. Blood components, especially erythrocytes, coagulation factors, complement and immunoglobulins, also have a role in causing secondary ICH-related injury. In fact, main effects of the inflammatory response and production of thrombin are the accumulation of cerebral edema in the early phases after the occurrence of ICH and the apoptosis of neuronal cells. Hemoglobin released from erythrocytes increases the production of free radicals, which contribute to oxidative damage, thus leading to cellular death. Hemin also greatly contributes to brain injury pathogenesis, by the excessive release of iron, the depletion of glutathione levels and the generation of free radicals. Secondary injury due to inflammatory response plays a pivotal role in worsening neurological deterioration in subjects with ICH.

The findings that are performed in SAH patients are broadly applicable to inflammatory mediated diseases because the ability to centrally reduce inflammatory cytokines in the CNS can mitigate a number of diseases where inflammation plays a central role such as Alzheimer disease, Parkinson disease, Amyotrophic lateral sclerosis, Cerebral ischemia, Traumatic brain injury, autoimmune disorders, meningitis, encephalitis, depression and psychiatric disorders, and epilepsy.

A key element to consider for the successful clinical implementation of taVNS is the manner in which it is deployed. Specifically, electrodes are often placed on the ear by mechanical force (i.e. clips) or dry electrode form factors requiring attention to application. Also the battery and electronics for the power and control of the simulation are often separate from the electrodes. Finally, the form factors for the technology are often non-disposable which can limit their deployability and ease of use. This is especially true in an intensive care unit clinical setting.

In some aspects, the method includes administering vagal nerve stimulation (VNS) to a patient in need. VNS can be accomplished non-invasively by stimulating the auricular branch of the vagus nerve in the ear. This transcutaneous auricular approach has demonstrated good efficacy. In one aspect, the transcutaneous stimulation of the auricular branch of the vagus nerve is implemented using a portable TENS (transcutaneous electrical nerve stimulation) unit connected to two ear clip electrodes positioned in an ear of the subject. Without being limited to any particular theory, the external ear is an effective position for non-invasive stimulation of the vagus nerve, where the auricular branch travels in the pinna of the ear. In one aspect, the ear clips used for the VNS treatment are positioned along the concha of the ear.

Figure 4:
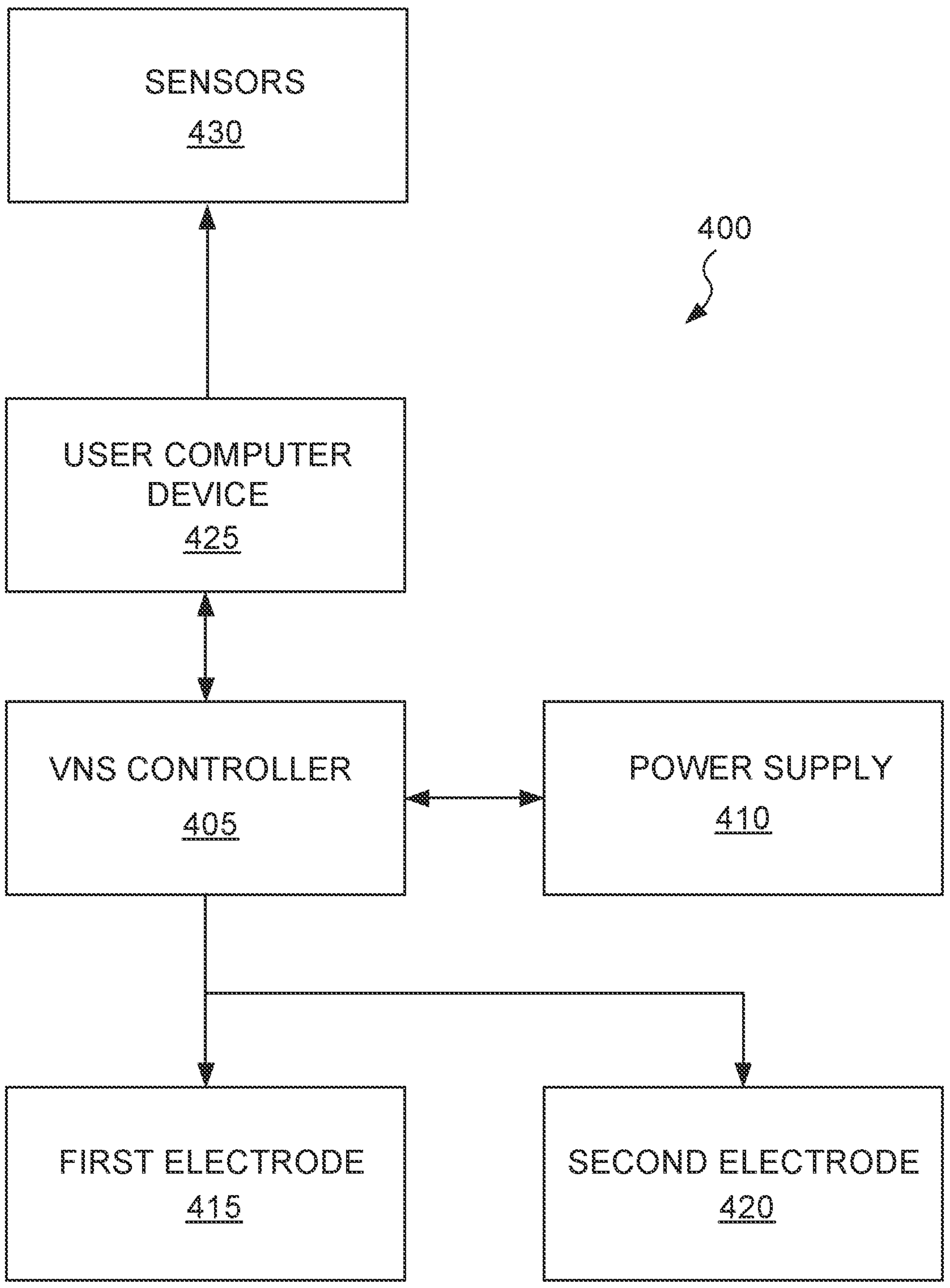
FIG. 4 illustrates a system for providing vagal nerve stimulation to a patient in accordance with at least one embodiment.

Generally, a safe and effective amount of vagal nerve stimulation (VNS) is, for example, an amount that would cause the desired therapeutic effect in a subject while minimizing undesired side effects FIG. 4 illustrates a system 400 for providing vagal nerve stimulation to a patient in accordance with at least one embodiment.

A current trend in neuromodulation is the use of vagus nerve stimulation (VNS) as a means to promote neuroplasticity. The vagus nerve, which is comprised of 80% afferent fibers and 20% efferent fibers, is the main visceral sensory nerve and innervates many organs throughout the body. Stimulating the vagus nerve is typically performed using surgically implanted cuff electrodes—encircling the left vagus nerve within the carotid sheath—that are connected to a pulse generator implanted in the left side of the patient's chest. The left vagus nerve is used because it has fewer efferent fibers descending to the heart than the right vagus nerve, making it a safer site for stimulation. VNS has been proven effective as a treatment for intractable epilepsy and treatment-resistant depression, and has recently been investigated for several neurological injuries such as stroke and traumatic brain injury.

The vagus nerve is known to have a direct ascending projection to the nucleus tractus solitarius (NTS) which in turn activates the locus coeruleus (LC) and nucleus basalis (NB). The LC (located in the pons) and NB (located in the basal forebrain) are part of a neuromodulatory system with diffuse projections throughout cortical and subcortical areas. The LC contains noradrenergic neurons (norepinephrine, NE), and the NB contains cholinergic neurons (acetylcholine, ACh), both of which are known to be plasticity-promoting neuromodulators. The releases of NE and ACh are important in processes such as arousal, memory encoding, and task-related behavior, as well as processes requiring high attentional load. Thus, NE and ACh could have an important role in the mechanism of action for VNS-paired rehabilitation involving goal-directed behavior.

VNS stimulation triggers bursts of NE and ACh neuromodulator release causing changes in cortical plasticity. It is thought that these changes in cortical plasticity may lead to the therapeutic effect. Specifically, VNS has been shown to lead to reorganization of rat auditory and motor cortex, with increased cortical representations of VNS-paired tones or movements, respectively. This is further supported by lesion studies that have shown that depleting NE or ACh concentrations leads to blocked cortical plasticity and impaired learning. VNS has the capability to improve human recognition memory when administered at a moderate intensity. VNS has also been shown to improve retention on the Hopkins Verbal Learning Test when delivered during the memory consolidation phase, as well as to enhance working memory evidenced by reduced error rates on an executive functioning task.

While invasive VNS has been studied for several decades, non-invasive stimulation of the vagus nerve, specifically the auricular branch, which innervates the cymba concha and tragus regions of the outer ear, has emerged as an exciting non-invasive alternative. Transcutaneous auricular VNS (taVNS) provides clear benefits in eliminating the need for an invasive surgery and reducing the possible side effects which come with an implanted device. Several functional magnetic resonance imaging (fMRI) studies have demonstrated taVNS has central effects similar to invasive VNS. In comparison to sham earlobe stimulation, stimulating the left cymba concha has been shown to result in significant activation of the central vagal projections, such as the NTS and LC. Another fMRI study comparing the cymba concha and tragus as sites for taVNS found that both locations activated vagal projections, but only the cymba concha led to significant activations of the NTS and LC when compared to sham stimulation. Stimulating the vagus nerve via the outer ear has been investigated for many similar conditions as its invasive counterpart, such as epilepsy, depression, and tinnitus. Furthermore, similar to findings from invasive VNS, taVNS has also been shown to have cognitive benefits such as improved speech category learning and retention of non-native language tone categories, as well as enhanced associative memory in older adults.

The system 400 includes a VNS controller 405. The VNS controller 405 can be a computer device, such as a tablet, laptop, desktop, or other dedicated computer device including at least one processor in communication with at least one memory device. The VNS controller 405 can also include a user interface that that allows the VNS controller 405 to present information to a user and receive user inputs.

The VNS controller 405 is in communication with a power supply 410 configured to provide electrical stimulation. The VNS controller 405 can also be in communication with one or more electrodes, such as a first electrode 415 and a second electrode 420. The first electrode 415 and the second electrode 420 are configured to provide the electrical stimulation to the patient. In some embodiments, first electrode 415 and second electrode 420 are permanent, re-usable electrodes. In other embodiments first electrode 415 and second electrode 420 are disposable, single use electrodes. In still further embodiments, one or more of the first electrode 415 and the second electrode 420 are implanted in the patient to stimulate the vagus nerve. In additional embodiments, the first electrode 415 and the second electrode 420 are temporarily attached to the patient's ear to stimulate the vagus nerve. In other embodiments, the first electrode 415 and the second electrode 420 provide electrical stimulation, vibration, or ultrasonic methods of activating the nerve, In at least one embodiment, the VNS controller 405 is configured to provide treatment to the vagus nerve by electrically stimulation for a period of twenty minutes. In at least one embodiment, the attributes of the electrical stimulation are 20 Hz, 250 μs, and 0.4 mA. In other embodiments, the current can range between 0.4 and 8 mA. The attributes of the electrical stimulation stay the same throughout the treatment. In at least one further embodiment, the electrical stimulation is performed twice a day. In at least one embodiment, the attributes of the electrical stimulation are selected to maximize vagus somatosensory evoked potentials while avoiding perception of pain.

In the exemplary embodiment, the VNS controller 405 controls the output of the power supply 410 to provide the electrical stimulation via the first electrode 415 and the second electrode 420.

In some further embodiments, VNS controller 405 is in communication with one or more user computer devices 425. The user computer device 425 may provide information to the VNS controller 405, such as one or more attributes of the patient that may alter the electrical stimulation applied to the patient. Furthermore, the user computer device 425 may provide timing information to the VNS controller 405, such as when to apply the electrical stimulation. Moreover, the user computer device 425 can receive information from the VNS controller 405, such as what were the attributes of the electrical stimulation that was applied to the patient.

The user computer device 425 can also be attached to one or more sensors 430. The sensors 430 can be used to determine the optimal taVNS parameters. In some embodiments, the sensors 430 may include, but are not limited to, electromyography (EMG). The sensors 430 may further monitor the overall health of the patient while undergoing the procedures described herein.

In some embodiments, the sensors 430 include stereotactic electroencephalography (sEEG). The sensors 430 can then be used to monitor the effects of stimulation parameters on the subject's brain activity, especially during motor tasks. During these tasks, the sensors 430 may report the effect of stimulation frequency, pulse-width, and current intensity on the subject's brain activity. This may be used to find ideal parameters and/or adjust parameters to each individual subject. Other sensors 430 can include, but are not limited to, temperature, brain wave activity, galvanic response, blood pressure, heart rate, and/or any other attribute or statistic of the patient that is desired.

In some embodiments, the user computer device 425 monitors the patient's brain activity and response to the taVNS stimulation. In some embodiments, the user computer device 425 adjusts the output of the VNS controller 405 to maximize the patient's results.

Figure 5:
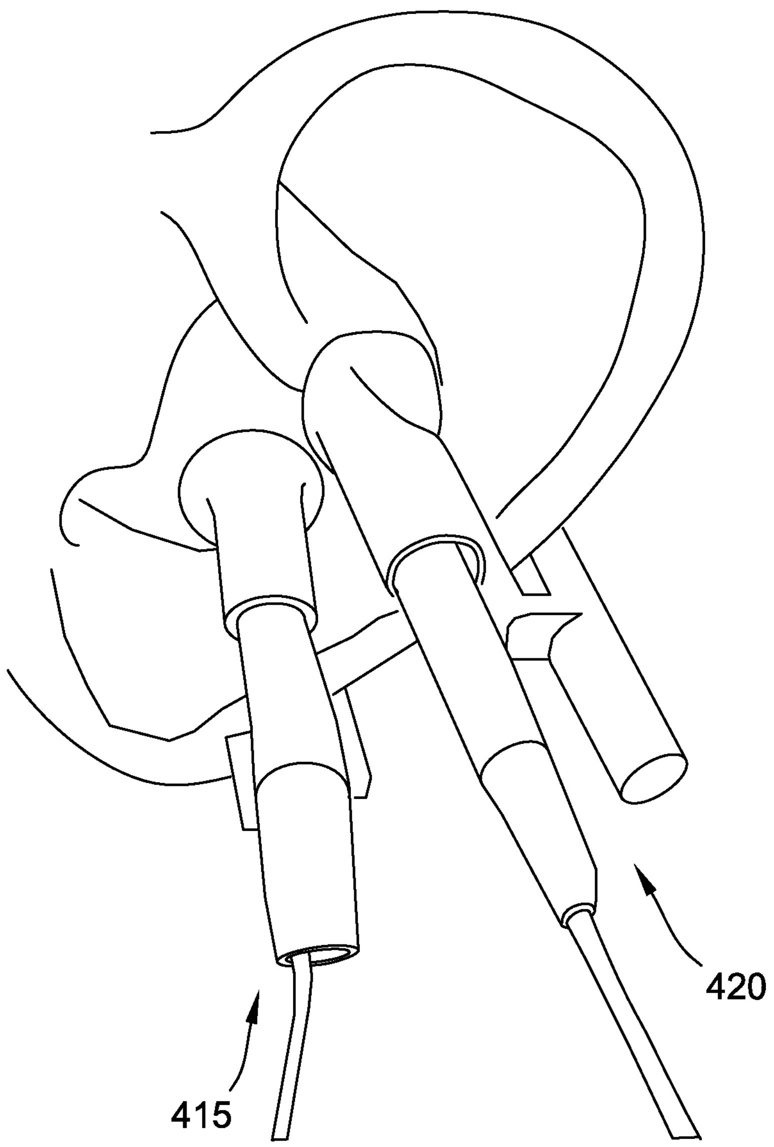
FIG. 5 illustrates placement of electrodes for non-invasive transcutaneous vagus nerve stimulation using the system shown in FIG. 6.

FIG. 5 illustrates placement of electrodes 415 and 420 (shown in FIG. 4) for non-invasive transcutaneous vagus nerve stimulation using the system 400 (shown in FIG. 4). In FIG. 5, the VNS controller 405 (shown in FIG. 1) is a part of a portable TENS (transcutaneous electrical nerve stimulation) unit. The TENS is connected to two the two electrodes 415 and 420.

In the exemplary embodiment, the first electrode 415 and the second electrode 420 are placed along the concha of the ear to stimulate the vagus nerve where the auricular branch travels in the pinna of the ear. In the exemplary embodiment, the first electrode 415 and the second electrode are attached to the patient's left ear.

Figure 6:
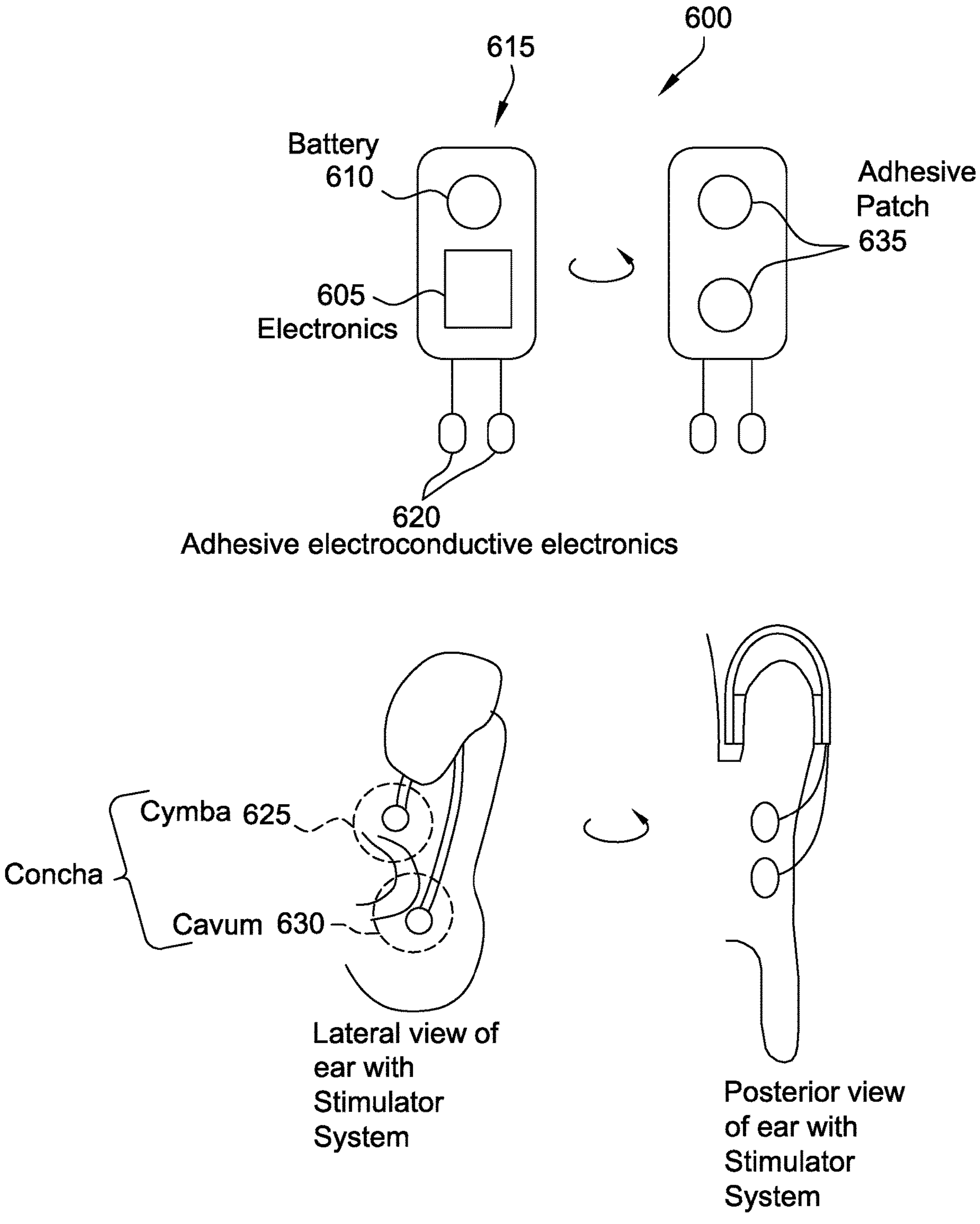
FIG. 6 illustrates diagrams of a system for performing transcutaneous auricular branch vagal nerve stimulation.

FIG. 6 illustrates diagrams of a system 600 for performing transcutaneous auricular branch vagal nerve stimulation. As illustrated in FIG. 6, the main body of the adherent system 600 contains electronics 605 and a power source 610 on a flexible substrate 615 that can be bent around the top of the ear (e.g. helix). Attached are electrodes 620 that have adhesive electroconductive gel electrodes that can be attached to the cymba 625 and cavum 630 of the concha. The system can also include one or more adhesive patches 635 to attach the flexible substrate 615 to the top of the ear. The system 600 has the capability to accommodate different sizes and geometries of ears. Further the system 600 enables easy application by a non-skilled health care provider.

In some embodiments, the system 600 could also stimulate auricular branch vagal nerve through providing vibration and/or ultrasound rather than, or in addition to, electrical current.

In at least one embodiment, the system 600 is configured to provide treatment to the vagus nerve by electrically stimulation for a period of twenty minutes. In at least one embodiment, the attributes of the electrical stimulation are 20 Hz, 250 μs, and 0.4 mA. In other embodiments, the current can range between 0.4 and 8 mA. The attributes of the electrical stimulation stay the same throughout the treatment. In at least one further embodiment, the electrical stimulation is performed twice a day. In at least one embodiment, the attributes of the electrical stimulation are selected to maximize vagus somatosensory evoked potentials while avoiding perception of pain.

Figure 7:
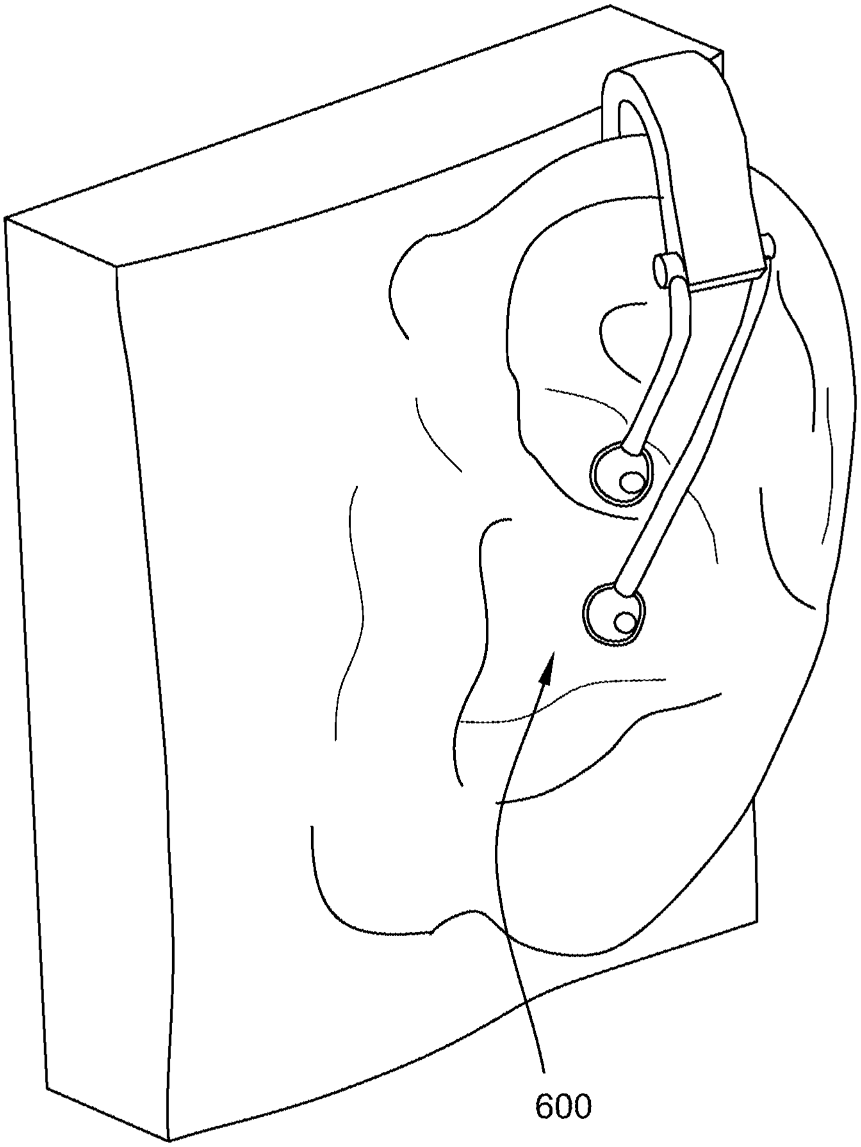
FIG. 7 illustrates a placement of a system for performing transcutaneous auricular branch vagal nerve stimulation.

FIG. 7 illustrates a placement of the system 600 (shown in FIG. 6) for performing transcutaneous auricular branch vagal nerve stimulation.

In the exemplary embodiment, the system 600 is configured to stimulate the auricular branch vagal nerve to reduce inflammation in the central nervous system, specifically the brain and spinal cord.

Figure 8:
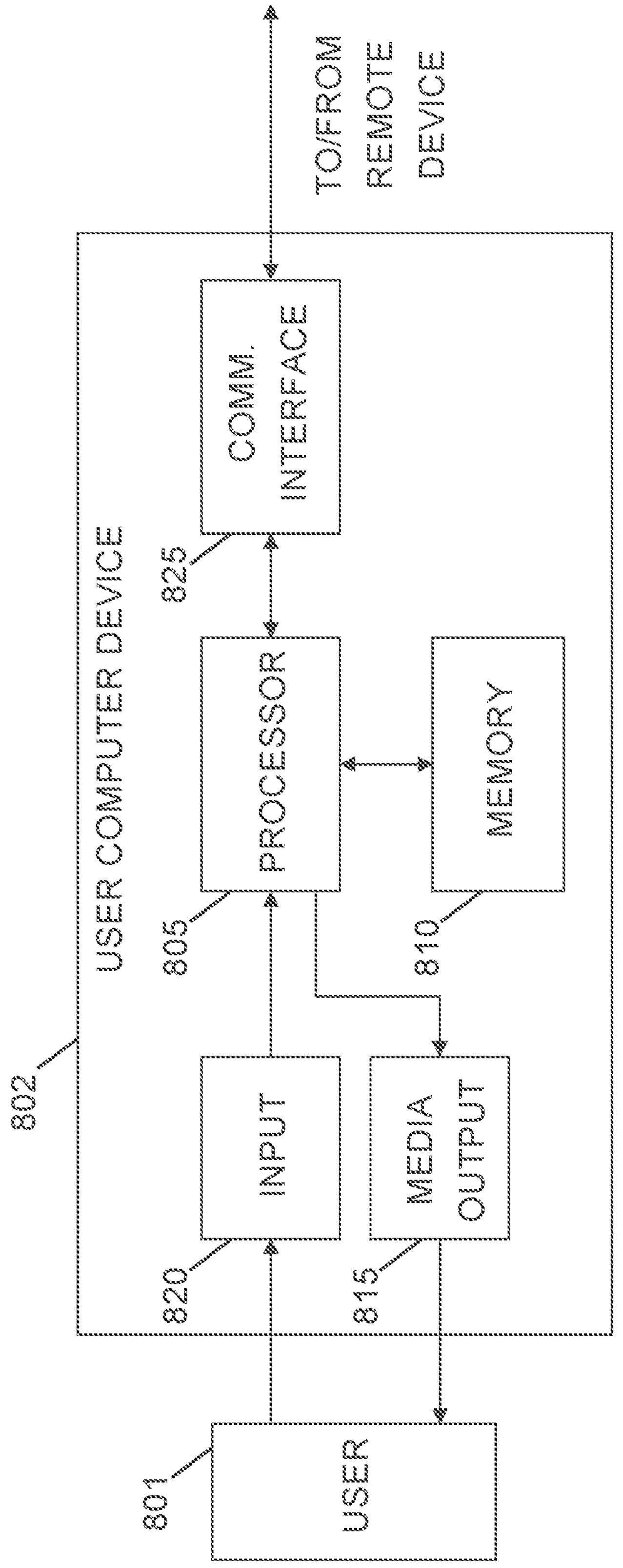
FIG. 8 illustrates an example configuration of a client system shown in FIG. 3, in accordance with one embodiment of the present disclosure.

FIG. 8 illustrates an example configuration of a client system shown in FIG. 4, in accordance with one embodiment of the present disclosure. User computer device 802 is operated by a user 801. User computer device 802 may include, but is not limited to, VNS controller 405 and user computer device 425 (both shown in FIG. 4). User computer device 802 includes a processor 805 for executing instructions. In some embodiments, executable instructions are stored in a memory area 810. Processor 805 may include one or more processing units (e.g., in a multi-core configuration) . Memory area 810 is any device allowing information such as executable instructions and/or transaction data to be stored and retrieved. Memory area 810 may include one or more computer-readable media.

User computer device 802 also includes at least one media output component 815 for presenting information to user 801. Media output component 815 is any component capable of conveying information to user 801. In some embodiments, media output component 815 includes an output adapter (not shown) such as a video adapter and/or an audio adapter. An output adapter is operatively coupled to processor 805 and operatively coupleable to an output device such as a display device (e.g., a cathode ray tube (CRT), liquid crystal display (LCD), light emitting diode (LED) display, or "electronic ink" display) or an audio output device (e.g., a speaker or headphones). In some embodiments, media output component 815 is configured to present a graphical user interface (e.g., a web browser and/or a client application) to user 801. A graphical user interface may include, for example, patient attributes or the attributes of the electrical stimulation. In some embodiments, user computer device 802 includes an input device 820 for receiving input from user 801. User 801 may use input device 820 to, without limitation, select to apply the electrical stimulation to the patient. Input device 820 may include, for example, a keyboard, a pointing device, a mouse, a stylus, a touch sensitive panel (e.g., a touch pad or a touch screen), a gyroscope, an accelerometer, a position detector, a biometric input device, and/or an audio input device. A single component such as a touch screen may function as both an output device of media output component 815 and input device 820.

User computer device 802 may also include a communication interface 825, communicatively coupled to a remote device such as a VNS controller 405 or a user computer device 425. Communication interface 825 may include, for example, a wired or wireless network adapter and/or a wireless data transceiver for use with a mobile telecommunications network.

Stored in memory area 810 are, for example, computer-readable instructions for providing a user interface to user 801 via media output component 815 and, optionally, receiving and processing input from input device 820. The user interface may include, among other possibilities, a web browser and/or a client application. Web browsers enable users, such as user 801, to display and interact with media and other information typically embedded on a web page or a website provided by a server. A client application allows user 801 to interact with, for example, VNS controller 405. For example, instructions may be stored by a cloud service and the output of the execution of the instructions sent to the media output component 815.

The methods and systems described herein may be implemented using computer programming or engineering techniques including computer software, firmware, hardware, or any combination or subset thereof, wherein the technical effects may be achieved by performing at least one of the following steps: a) attaching a stimulation device to the patient's ear, wherein the stimulation device includes a first electrode to be attached to a cymba of a patient's ear and a second electrode to be attached to a cavum of the patient's ear, wherein the patient's ear is a left ear; b) stimulating a cutaneous distribution of a patient's vagus nerve within the patient's ear with a nerve stimulating signal via the stimulation device, wherein the stimulating signal is provided to the auricular branch of the vagus nerve where the vagus nerve travels in the pinna of the ear, wherein the stimulating signal is electrical stimulation of the vagus nerve or wherein the stimulating signal is vibrotactile stimulation of the vagus nerve, wherein the stimulating signal is provided for twenty minutes, wherein the system is disposable upon conclusion of the stimulating signal.

A computer program of one embodiment is embodied on a computer-readable medium. In an example, the system is executed on a single computer system, without requiring a connection to a server computer. In a further example embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). In a further embodiment, the system is run on an iOS® environment (iOS is a registered trademark of Cisco Systems, Inc. located in San Jose, CA). In yet a further embodiment, the system is run on a Mac OS® environment (Mac OS is a registered trademark of Apple Inc. located in Cupertino, CA). In still yet a further embodiment, the system is run on Android® OS (Android is a registered trademark of Google, Inc. of Mountain View, CA). In another embodiment, the system is run on Linux® OS (Linux is a registered trademark of Linus Torvalds of Boston, MA). The application is flexible and designed to run in various different environments without compromising any major functionality. In some embodiments, the system includes multiple components distributed among a plurality of computing devices. One or more components are in the form of computer-executable instructions embodied in a computer-readable medium. The systems and processes are not limited to the specific embodiments described herein. In addition, components of each system and each process can be practiced independently and separately from other components and processes described herein. Each component and process can also be used in combination with other assembly packages and processes.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit (ASIC), and other programmable circuits, and these terms are used interchangeably herein. In the embodiments described herein, memory may include, but is not limited to, a computer-readable medium, such as a random-access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable and include any computer program storage in memory for execution by personal computers, workstations, clients, servers, and respective processing elements thereof.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device, and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Furthermore, as used herein, the term "real-time" refers to at least one of the time of occurrence of the associated events, the time of measurement and collection of predetermined data, the time for a computing device (e.g., a processor) to process the data, and the time of a system response to the events and the environment. In the embodiments described herein, these activities and events may be considered to occur substantially instantaneously.

The aspects described herein may be implemented as part of one or more computer components, such as a client device, system, and/or components thereof, for example. Furthermore, one or more of the aspects described herein may be implemented as part of a computer network architecture and/or a cognitive computing architecture that facilitates communications between various other devices and/or components. Thus, the aspects described herein address and solve issues of a technical nature that are necessarily rooted in computer technology.

A processor or a processing element may be trained using supervised or unsupervised machine learning, and the machine learning program may employ a neural network, which may be a convolutional neural network, a deep learning neural network, a reinforced or reinforcement learning module or program, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics and information, traffic timing, previous trips, and/or actual timing. The machine learning programs may utilize deep learning algorithms that may be primarily focused on pattern recognition, and may be trained after processing multiple examples. The machine learning programs may include Bayesian Program Learning (BPL), voice recognition and synthesis, image or object recognition, signal processing, optical character recognition, and/or natural language processing—either individually or in combination. The machine learning programs may also include natural language processing, semantic analysis, automatic reasoning, and/or machine learning.

Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. In one embodiment, machine learning techniques may be used to determine brain responses to stimuli such as VNS settings.

Based upon these analyses, the processing element may learn how to identify characteristics and patterns that may then be applied to analyzing image data, model data, and/or other data. For example, the processing element may learn, to identify brain responses to stimuli and the VNS settings for different patients to provide optimal gamma activity. The processing element may also learn how to identify trends that may not be readily apparent based upon collected traffic data, such as trends that identify when gamma activity will spike or decline.

The exemplary systems and methods described and illustrated herein therefore provide VNS treatments for changing neuroplasticity, altering parasympathetic tone, reducing seizures, immunomodulation, or reducing inflammation.

The computer-implemented methods and processes described herein may include additional, fewer, or alternate actions, including those discussed elsewhere herein. The present systems and methods may be implemented using one or more local or remote processors, transceivers, and/or sensors (such as processors, transceivers, and/or sensors mounted on vehicles, stations, nodes, or mobile devices, or associated with smart infrastructures and/or remote servers), and/or through implementation of computer-executable instructions stored on non-transitory computer-readable media or medium. Unless described herein to the contrary, the various steps of the several processes may be performed in a different order, or simultaneously in some instances.

Additionally, the computer systems discussed herein may include additional, fewer, or alternative elements and respective functionalities, including those discussed elsewhere herein, which themselves may include or be implemented according to computer-executable instructions stored on non-transitory computer-readable media or medium.

In the exemplary embodiment, a processing element may be instructed to execute one or more of the processes and subprocesses described above by providing the processing element with computer-executable instructions to perform such steps/sub-steps, and store collected data (e.g., trust stores, authentication information, etc.) in a memory or storage associated therewith. This stored information may be used by the respective processing elements to make the determinations necessary to perform other relevant processing steps, as described above.

The aspects described herein may be implemented as part of one or more computer components, such as a client device, system, and/or components thereof, for example. Furthermore, one or more of the aspects described herein may be implemented as part of a computer network architecture and/or a cognitive computing architecture that facilitates communications between various other devices and/or components. Thus, the aspects described herein address and solve issues of a technical nature that are necessarily rooted in computer technology.

Although specific features of various embodiments may be shown in some drawings and not in others, this is for convenience only. In accordance with the principles of the systems and methods described herein, any feature of a drawing may be referenced or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a programmable logic unit (PLU), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

The computer-implemented methods discussed herein may include additional, less, or alternate actions, including those discussed elsewhere herein. The methods may be implemented via one or more local or remote processors, transceivers, servers, and/or sensors, and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system for transcutaneous auricular branch vagal nerve stimulation comprising:
- a first electrode to be attached to a first location in a concha of a patient's ear;
- a second electrode to be attached to a second location in the concha of the patient's ear; and
- a flexible substrate configured to be bent over a helix of the patient's ear to secure the system to the patient's ear, the flexible substrate including:
  - a first adhesive patch to secure the system to the patient's ear, the first adhesive patch to be adhered to a first side of the patient's ear; and
  - a second adhesive patch to secure the system to the patient's ear to be adhered to a second side of the patient's ear.

2. The system of claim 1, wherein the flexible substrate includes a first surface and a second surface, and the first adhesive patch and the second adhesive patch are on the first surface of the flexible substrate and the system further comprising a battery and electronics attached to the second surface the flexible substrate.

3. The system of claim 2, wherein the first electrode and the second electrode transmit at least one of electrical current, vibration, or ultrasonic waves to stimulate an auricular branch of a vagus nerve.

4. The system of claim 3, wherein the stimulation provokes a therapeutic effect of reducing inflammation.

5. The system of claim 4, wherein the therapeutic effect is reducing inflammation in a central nervous system.

6. The system of claim 3, wherein the stimulation occurs for twenty minutes.

7. The system of claim 1, wherein the system is disposable upon conclusion of the stimulation.

8. The system of claim 1, wherein the flexible substrate is bent over a top of the patient's ear to secure the system to the patient's ear.

9. The system of claim 1, wherein the first electrode and the second electrode further comprise an adhesive to attach the first electrode and the second electrode to the patient's ear.

10. A method for transcutaneous auricular branch vagal nerve stimulation to reduce inflammation in a central nervous system of a patient, the method comprising:
- attaching a neuromodulation device to an ear of the patient who has experienced an acute brain injury, the acute brain injury associated with a secondary inflammatory brain injury, the attaching the neuromodulation device including:
  - attaching an adhesive of the neuromodulation device behind a helix of the ear;
  - attaching a first electrode of the neuromodulation device to a first location in a concha of the ear; and
  - attaching a second electrode of the neuromodulation device to a second location in the concha of the ear; and
- stimulating a cutaneous distribution of a vagus nerve of the patient within the ear with a nerve stimulating signal via the first electrode and the second electrode to mitigate neurological deterioration in the patient by modulation inflammatory signaling associated with the secondary inflammatory brain injury following the acute brain injury.

11. The method of claim 10, wherein the attaching of the neuromodulation device to the ear includes attaching the neuromodulation device to a left ear of the patient.

12. The method of claim 10, wherein the nerve stimulating signal is electrical stimulation of the vagus nerve.

13. The method of claim 10, wherein the nerve stimulating signal is vibrotactile stimulation of the vagus nerve.

14. The method of claim 10, wherein the nerve stimulating signal is provided to an auricular branch of the vagus nerve.

15. The method of claim 10, wherein the nerve stimulating signal is provided for twenty minutes.

16. The method of claim 10, wherein the neuromodulation device is disposable upon conclusion of the nerve stimulating signal.

17. The method of claim 10, wherein the acute brain injury includes at least one of an ischemic stroke, a cerebral hemorrhage, or a traumatic brain injury.

18. The method of claim 10, wherein the secondary inflammatory brain injury includes at least one of a cerebral edema or a cerebral ischemia.

19. A disposable device for transcutaneous auricular branch vagal nerve stimulation to reduce inflammation in a central nervous system of a patient, the device comprising:

an electrical stimulation device including:

two electrodes;

a battery; and an adhesive configured to attach the device to an ear of the patient, the adhesive configured to be placed behind a helix of the patient's ear, wherein the electrical stimulation device is configured to provide an electrical current to a patient's vagus nerve with an electrical signal for twenty minutes, wherein the electrical signal is configured to stimulate a cutaneous distribution of a vagus nerve of the patient within the ear with a nerve stimulating signal.

* * * * *